(12) United States Patent
Hajizadeh et al.

(10) Patent No.: US 11,382,757 B1
(45) Date of Patent: Jul. 12, 2022

(54) CONDYLAR ASYMMETRY KNEE PROSTHESIS

(71) Applicant: Lento Medical Inc., Houston, TX (US)

(72) Inventors: Khatereh Hajizadeh, San Jose, CA (US); Ilwhan Park, Katy, TX (US)

(73) Assignee: LENTO MEDICAL, INC., Houston, TX (US)

( * ) Notice: Subject to any disclaimer, the term of this patent is extended or adjusted under 35 U.S.C. 154(b) by 0 days.

(21) Appl. No.: 17/150,174

(22) Filed: Jan. 15, 2021

Related U.S. Application Data

(60) Provisional application No. 62/961,337, filed on Jan. 15, 2020.

(51) Int. Cl.
*A61F 2/38* (2006.01)
*A61F 2/30* (2006.01)

(52) U.S. Cl.
CPC .......... *A61F 2/3859* (2013.01); *A61F 2/389* (2013.01); *A61F 2/3886* (2013.01); *A61F 2002/30131* (2013.01)

(58) Field of Classification Search
CPC ....... A61F 2/389; A61F 2/3859; A61F 2/3868
See application file for complete search history.

(56) References Cited

U.S. PATENT DOCUMENTS

| | | | |
|---|---|---|---|
| 7,326,252 B2* | 2/2008 | Otto | ............... A61F 2/3886 623/20.15 |
| 7,998,203 B2 | 8/2011 | Blum | |
| 8,403,994 B2 | 3/2013 | Maloney et al. | |
| 9,023,111 B2 | 5/2015 | Walker | |
| 9,730,810 B2 | 8/2017 | Fisher et al. | |
| 9,744,044 B2 | 8/2017 | Cohen et al. | |
| 10,045,853 B2* | 8/2018 | Fiedler | ............... A61F 2/3859 |
| 2009/0319049 A1 | 12/2009 | Shah et al. | |
| 2009/0326666 A1* | 12/2009 | Wyss | ............... A61F 2/3886 623/20.29 |
| 2009/0326667 A1* | 12/2009 | Williams | ............... A61F 2/3868 623/20.31 |
| 2013/0296860 A1 | 11/2013 | Chana et al. | |

(Continued)

FOREIGN PATENT DOCUMENTS

WO     WO2001070143 A1     9/2001

*Primary Examiner* — Jason-Dennis N Stewart
(74) *Attorney, Agent, or Firm* — Mark Protsik; Thomas Schneck

(57) ABSTRACT

A knee prosthesis for total knee replacement has femoral and tibial joint components. The femoral component has a medial condyle, a lateral condyle and an intercondylar recess between the condyles. The condyles in sagittal profile both have spiral outer surfaces, wherein the increasing anterior-to-posterior radii of curvature for the medial condyle is smaller than the corresponding radii of curvature for the lateral condyle. The tibial component has shallow concave medial and lateral condyle surfaces for receiving corresponding condyles of the femoral component as bearing surfaces when the femoral and tibial components are biased together under applied tension by ligaments. Posterior portions of each femoral condyle that contact the corresponding tibial condyle up to 90° flexion are substantially spherical in shape, with gradually increasing radii in coronal profile as flexion increases, while the anterior portions beyond 90° flexion are substantially elliptical in shape in coronal profile.

11 Claims, 7 Drawing Sheets

(56) References Cited

U.S. PATENT DOCUMENTS

2018/0021144 A1* 1/2018 Parisi .................. A61F 2/389
 623/20.32
2021/0113340 A1* 4/2021 Parisi .................. A61F 2/389

* cited by examiner

CONDYLAR ASYMMETRY KNEE PROSTHESIS

CROSS-REFERENCE TO RELATED APPLICATION

The present application claims priority under 35 U.S.C. 119(e) from U.S. provisional application No. 62/961,337 filed Jan. 15, 2020.

TECHNICAL FIELD

The present invention relates to a knee prosthesis for implanting in total knee replacement surgery.

BACKGROUND ART

Knee joint motion, i.e., interaction between the distal end of the femur and the proximal end of the tibia during flexion and extension, is quite complex. While it might seem that the tibia merely rotates relative to the femur about a sagittal axis passing through the knee, there are also longitudinal rotations of the tibia relative to the femur as well as translational motions between femur and tibia. The complex knee articulation is determined by the geometry of the distal femur and proximal tibia and the arrangement of ligaments that hold the femur and tibia together.

Current prosthetic implants for total knee replacement generally do not fully address the complexity of knee joint motion. FIG. 1 shows an existing knee implant of the prior art. Instead, most of the existing implants have simple hinge-based designs providing for only anterior-posterior rotation, which limits the amount of flex to an average of only 70° to 80°. This limited flexion typically reduces a patient's quality of life after surgery.

What is needed is a knee prosthesis that more closely replicates a real knee's motion, accommodating not only a hinge-rotation motion of a knee joint, but also translation and lateral rotation of that knee joint to allow for greater flexion.

Also needed is a knee prosthesis that compensates for minor positioning errors that occur in surgery (mainly internal and external rotations of the femoral and tibial components).

SUMMARY DISCLOSURE

A knee replacement prosthesis comprises a femoral component and a tibial component that together enable anterior-posterior translation of the femur relative to the tibia and also enable the tibia to rotate about its longitudinal axis during flexion of the knee. The femoral component connects to the distal end of a resected femur and includes medial and lateral condyles having distal, articulating surfaces, and a patellar flange having a patellar articulating surface. The tibial component connects to the proximal end of a resected tibia and includes a proximal bearing surface with medial and lateral concavities that articulate with the medial and lateral condyles. Respective curvatures of the medial and lateral articulating surfaces are asymmetric to facilitate the axial rotation and anterior-posterior translation.

DETAILED DESCRIPTION

The present invention differs from previous designs in that it mimics natural knee movement by being able to simultaneously rotate and translate after passing 90° flex. The curvature on the lateral side makes the femoral component rotate after 90° flex and the curvature on the medial side blocks the tibial curvature to rotate out of range. The different radii of the femoral component in coronal plane accommodate rotation as the knee bends beyond 90° flexion and the medial collateral ligament (MCL) and the anterior cruciate ligament (ACL) are loose. Due to these features and different radii in the femoral component, the degree of rotation as the knee implant flexes is increased compared to prior designs.

Another feature on the medial side of the tibial component constrains the femoral component while it rotates to make it stable. Specifically, the profiles at the lateral and medial sides, as well as the curvatures on the anterior and posterior sides of tibial component provide the stability of the knee implant during fully extension and fully flexion positions. Therefore, in this invention, while we have a higher range of rotation, it is stable as well.

Still further, specific curvatures on the tibial component allow it to accommodate placement error up to 3° axial rotation of either component. To achieve this goal, we have two features on the tibial component which accommodate femur misplacement.

The implant size will be selected based upon medial-lateral (ML) and anterior-posterior (Ap) measurements which come from a patient's MRI or CT. Providing a wide range of different component sizes successfully addresses any issue regarding matching to a patient's anatomy.

Figure 1:
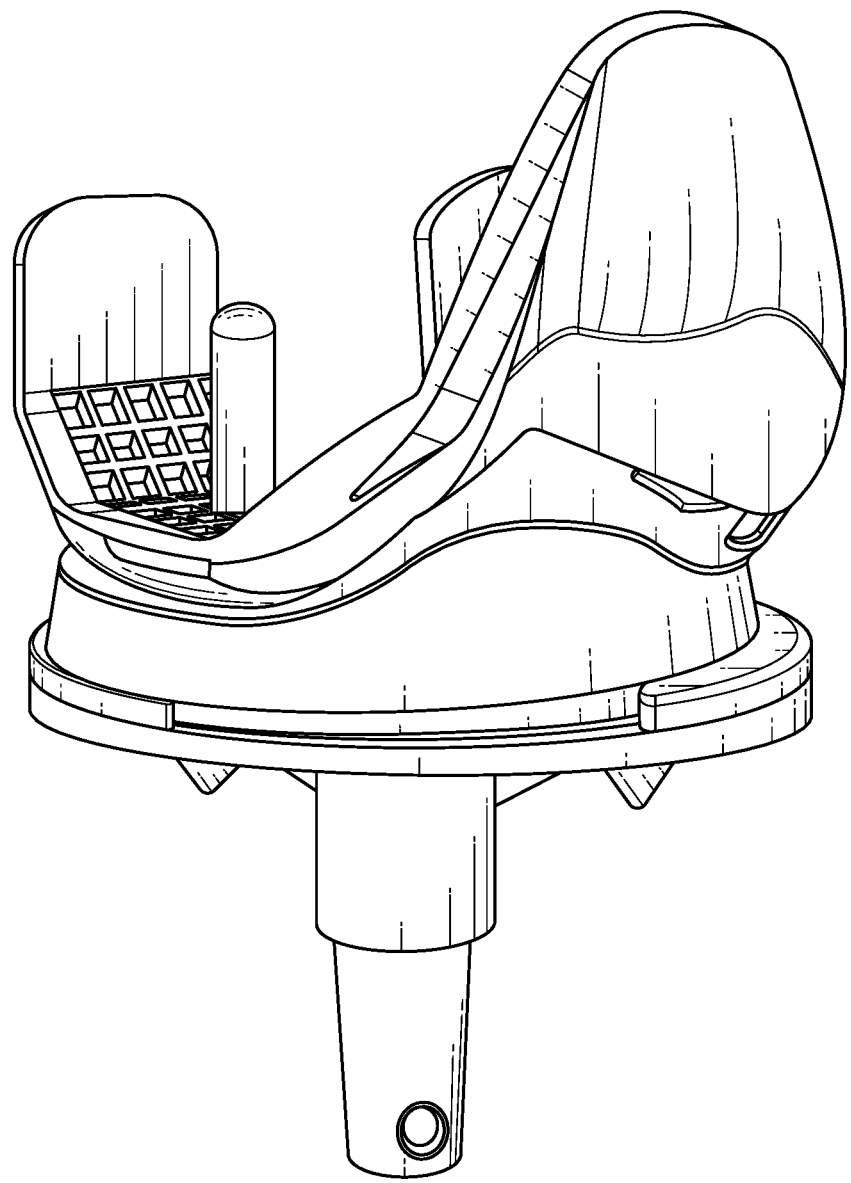
FIG. 1 is a perspective view of a knee implant of the prior art.
Figure 2:
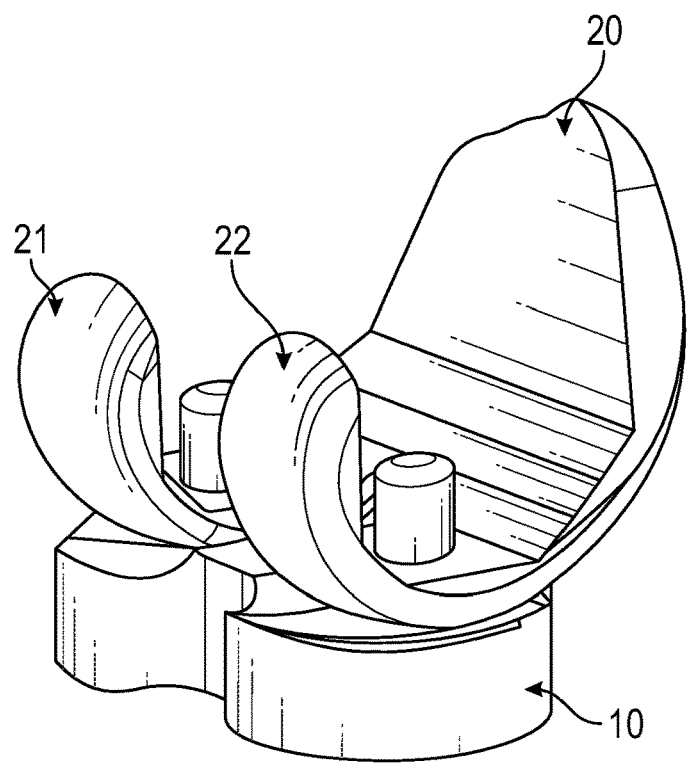
FIG. 2 is a perspective of a knee prosthesis in full extension in accordance with an embodiment of the invention showing the proximal surface of the femoral component.
Figure 3:
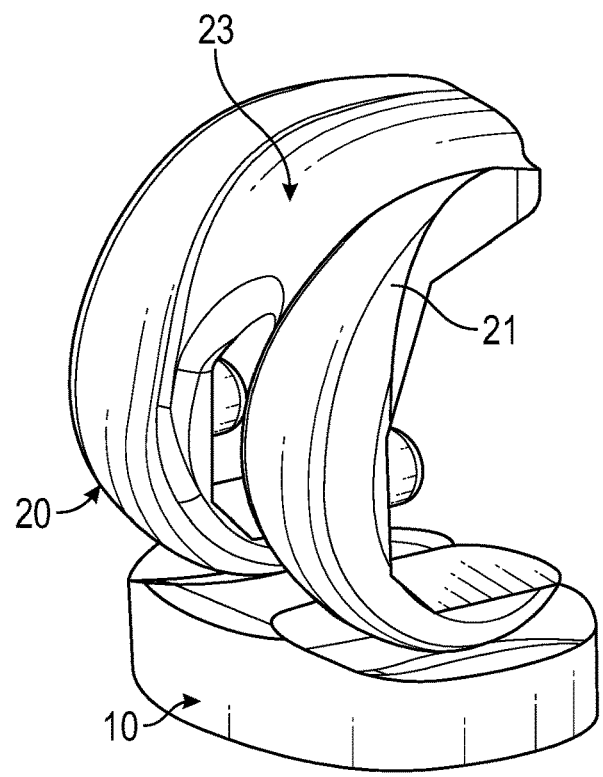
FIG. 3 is a perspective of a knee prosthesis in full flexion in accordance with an embodiment of the invention showing anterior condylar portion and Implant trochlear groove of the femoral component.

A knee replacement prosthesis in accordance with an embodiment of the invention is illustrated in FIGS. 2-9. In FIG. 2, the knee prosthesis is shown in its full extension position, while in FIG. 3, it is shown in 90° flex position. The prosthesis includes a femoral component 20, constructed and designed to be fixed to the distal end of a resected femur, and a tibial component 10, constructed and designed to be fixed to the proximal end of a resected tibia. The tibial component 10 and the femoral component 20 both have an asymmetrical design in coronal profile that can mimic knee natural motion. An implant trochlear groove 23, which bridges the anterior ends of the medial 21 and lateral 22 condyles, can be seen in FIG. 3.

The knee prosthesis that is illustrated in FIGS. 2-9 is for installation on the right knee. A mirror image (about the midpoint in coronal view) of the tibial and femoral components 10 and 20 will be used for installation on the left knee. The femoral component 20 has a medial condyle 21 and a lateral condyle 22. As the prosthesis flexes, different sections of the curved condylar portions engage and articulate with the tibial component 10.

Figure 4:
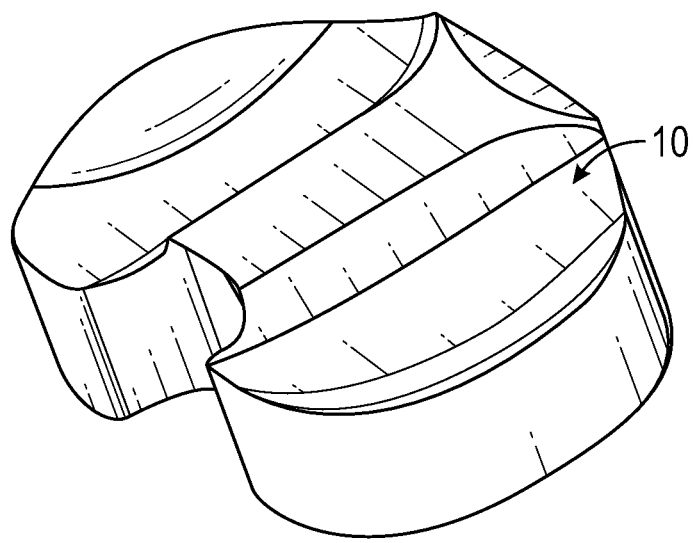
FIG. 4 is an enlarged perspective showing the tibial component 10.
Figure 5:
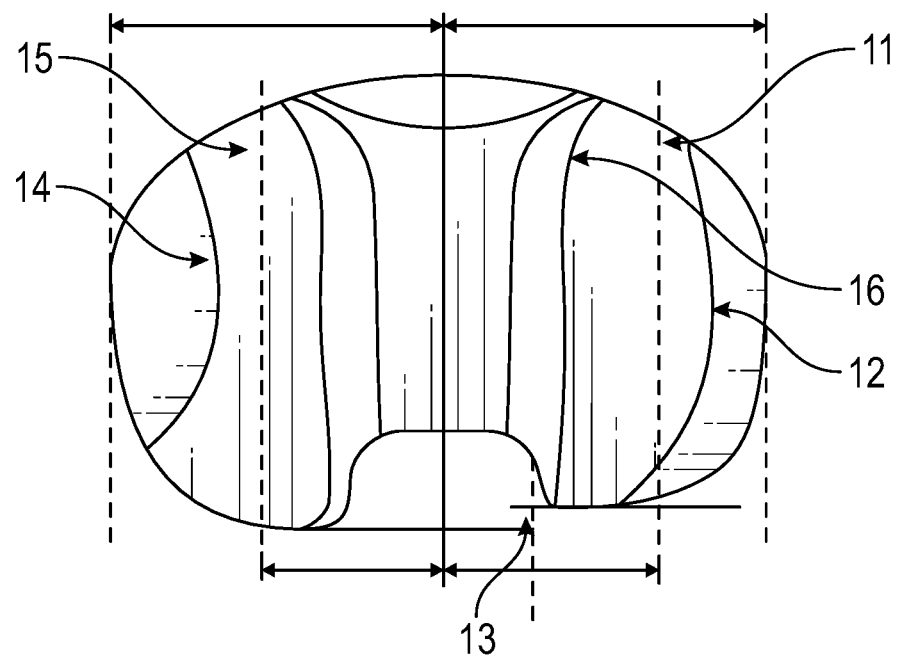
FIG. 5 is an enlarged perspective showing the side view of the tibial component 10.

FIGS. 4-5 show a schematic representation of the tibial component of the current invention. The tibial profile includes three specific curvatures in its design. A lateral side curvature 12 makes the femoral component rotate after 90° flex and a medial side curvature 14 limits the rotation of the femoral component according to the natural safe range of knee motion. The middle curvature 16 accommodates misplacement error of the femoral component. These curvatures on the axial plane all work together to accommodate a 3 to 5° misplacement error. This feature also accommodates enough space for femur rotation while knee flexes. Contact lines on the lateral side 11 and on the medial side 15 are shown in this FIG. 5 as well. The tibial lateral side is smaller than the tibial medial side. The radius of the curvature 12 on the posterior side is equal to the radius of the femur posterior condyle curvature in sagittal plane. This makes the femur rotate on the tibial part like a ball-and-socket joint. In other words, posterior condyles have a shape close to a sphere after 90° flex.

In real knees, the ACL causes the rotation of the knee after 90° knee flex position. In total knee replacement, the ACL is gone and with the help of a lateral curve feature 12 in this knee prosthesis, the rotation of the femur component is triggered, and the rest of the rotation will be taken care by patella ligaments. This feature can help the design rotate 20° to 30° beyond the 90° flex position. Medial curvature 14 blocks the femur from dislocation when the femur component rotates beyond 90-degree flex.

Figure 6:
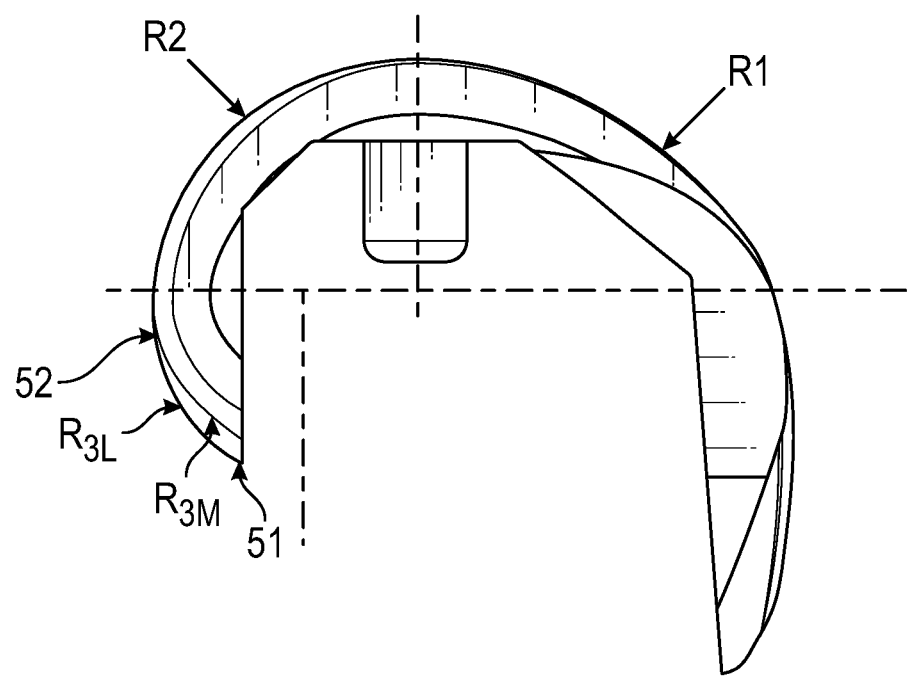
FIG. 6 is a lateral elevation of the femoral component 20.

FIG. 6 shows the femoral component in a sagittal view. The radii ($R_i$) of the femoral component are seen to gradually increase from its posterior to its anterior end in a manner approximating a logarithmic spiral. The radii of the femoral component ($R_i$) are a function of Ø, ML and AP parameters in the sagittal plane. Ø can range from 0.5 to 0.7, based on the size of the femur. Ø will be driven from the best Fibonacci number which is fitted to the anatomical knee data (AP and ML). n is the Fibonacci number, which may range from 4 to 10, and $f_n$ is the $n^{th}$ Fibonacci series value.

$$\emptyset = f_{n+1}/f_{n-1}, \text{ where } 4<n<10$$

$$R_i = F_r(\varphi, ML, AP)$$

The medial condyle radius 52 ($R_{3M}$) is smaller than the lateral condyle radius 51 ($R_{3L}$). Each condyle 21, 22 generally comprises an anterior and posterior surface, which blend smoothly with each other without any abrupt transition. In general, the major radius of curvature of the condyles 21, 22 varies from front to back to mimic anatomic femoral rollback during high degrees of flexion.

Figure 7:
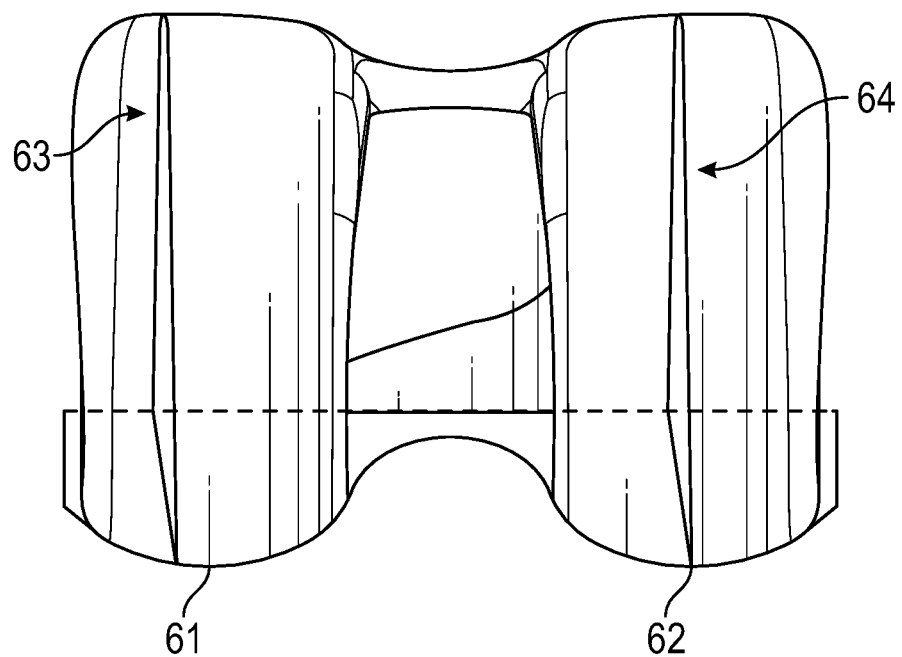
FIG. 7 is showing the condyles curvatures and contact points on lateral and medial sides of femoral component.
Figure 8A:
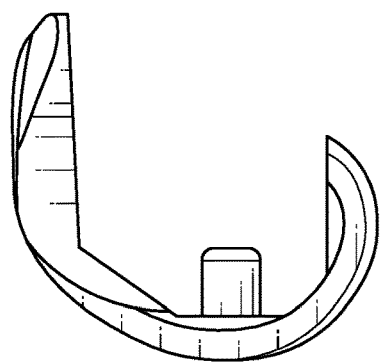
FIGS. 8(a)-8(e) and 9(a)-9(e) are respective sagittal and coronal views of the knee prosthesis that illustrate how the contact curvature gradually changed from a fully extended knee to a fully flexed knee position.
Figure 9A:
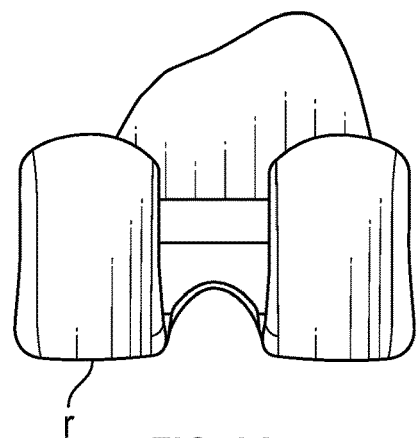
Figure 8B:
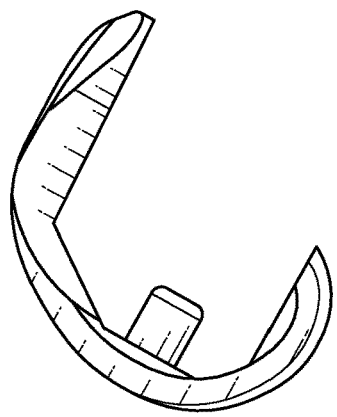
Figure 9B:
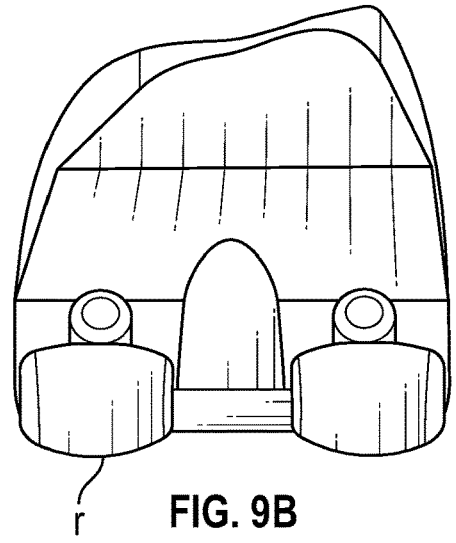
Figure 8C:
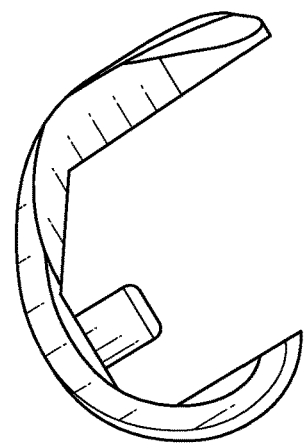
Figure 9C:
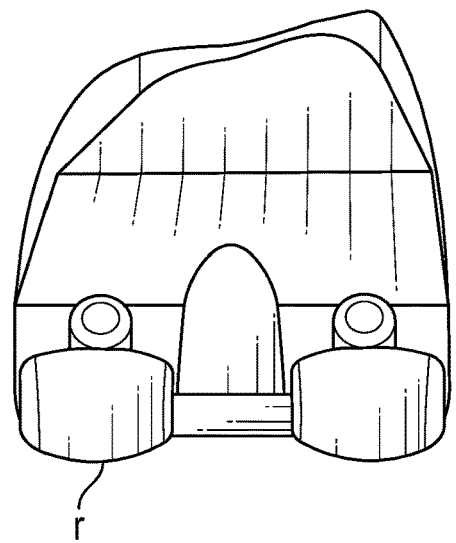
Figure 8D:
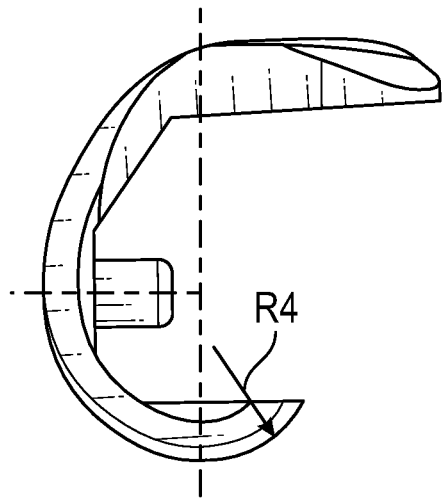
Figure 9D:
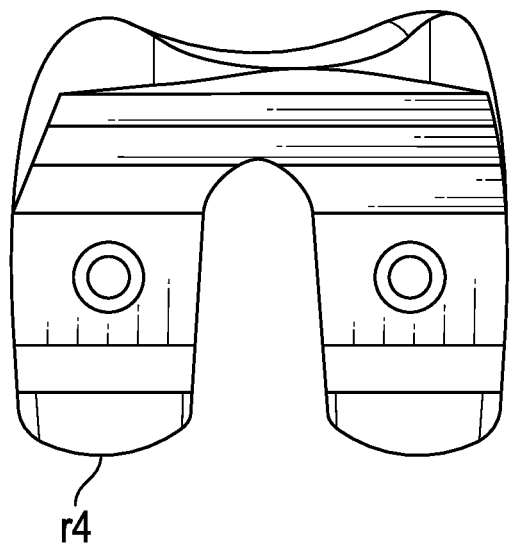
Figure 8E:
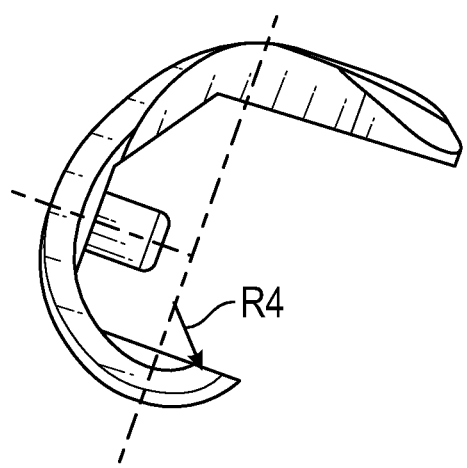
Figure 9E:
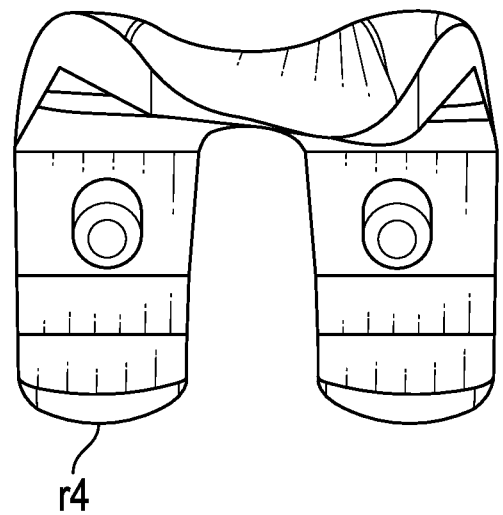

FIG. 7 shows femur condyles curvature in longitudinal view. The lateral condyle contact point 61 is moved to the side compared to the medial condyle contact point 62. This feature will help the femur rotate when it reaches 90° flexion to make the knee movement more natural and flexible. The contact points on lateral and medial side are traceable with lateral contact line 63 and medial contact line 64.

FIGS. 8(a)-(e) and 9(a)-(e) show the femoral component for varying degrees of flexion. In this invention, without loss of any anatomical shape, the curvature (radius r) of each condylar surface in coronal view changes from posterior to anterior. This affects how the femoral component articulates with the tibial component. The prior designs mostly have same radius circle-based feature on the femur component. The circle shape in proximal part allows rotation when the knee is 90-degree flex. The radius r will be selected as a function of the anatomical knee size and the rotation of the knee. It gives the implant higher flexibility compare to prior designs.

The radius of curvature of the condyle portion making contact gradually changes as the knee goes from zero to 90° flexion. When it reaches 90° flex, the radius r4 thereafter remains constant. And the radius r4 is equal to the radius of R4 in sagittal condyle view. Posterior condyles have a shape close to spherical after 90° flex.

The contact radius gradually changes when the femur rotates from a fully extended position (0°) to full flexion (110°). This contact radius variation helps the femur mimics natural knee movement. The posterior part of femoral condyle is spherical in shape, while the inferior part of femoral condyle is ellipsoidal in shape.

$$R = a_1 + a_2 \cdot f_1(\text{size}, \theta);$$

$$0.01 < a_1 < 0.2;$$

$$0.001 < a_2 < 0.1;$$

$f_1$ is the function of the anatomical size; and
$\theta$ is the rotation of the knee implant.

Figure 10A:
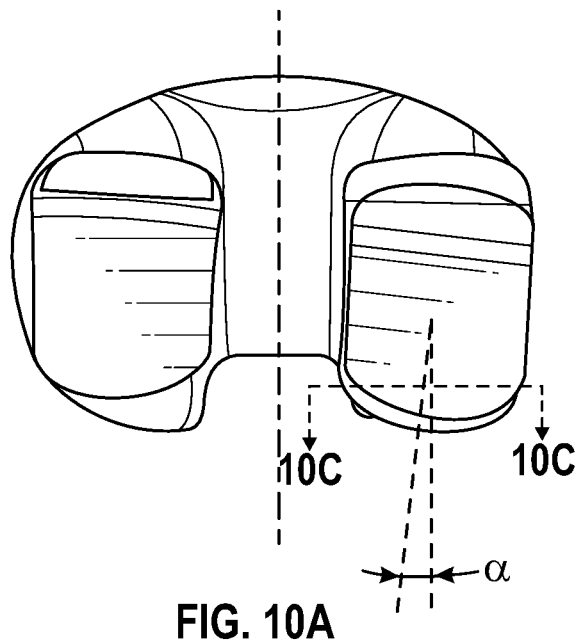
FIGS. 10(a)-10(b) are respective perspective and end views of the femoral component illustrating with a rotation in full knee flexion illustrating femoral axial rotation and displacement.
Figure 10B:
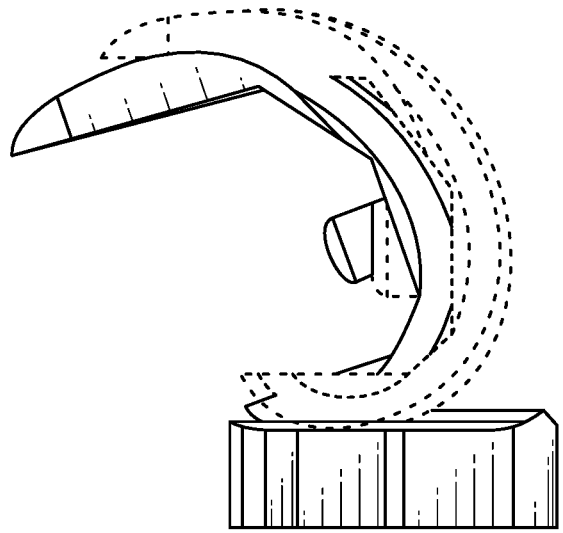
Figure 10C:
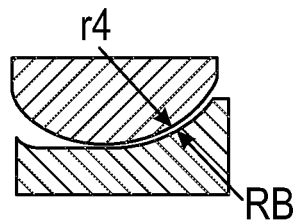
FIG. 10(c) is a sectional view taken along the line 10C-10C in FIG. 10(a).

FIGS. 10(a)-10(c) show how the tibia lateral side curvature and the femoral lateral condyle make the rotation after 90° flex. The rotation angle, α, is selected to be between 1° to 6°, based on the size of the implant and the knee movement. FIG. 10(c) also shows that the posterior lateral portion is close to sphere shape which trigger the rotation movement at the flex position.

The invention claimed is:

1. A knee prosthesis, comprising:
   a femoral joint component for attachment to a distal femur end, the femoral component having a medial condyle, a lateral condyle and an intercondylar recess between the condyles; and
   a tibial joint component for attachment to a proximal tibia end, the tibial component having shallow concave medial and lateral condyle surfaces for receiving corresponding condyles of the femoral component as bearing surfaces when the femoral and tibial components are biased together under applied tension by ligaments;
   the tibial joint component being lateral-medial mirror asymmetric in coronal profile, the medial and lateral condyles of the femoral joint component in sagittal profile both having spiral outer surfaces with increasing anterior-to-posterior radii of curvature, the increasing radii of curvature for the medial condyle being smaller than the corresponding radii of curvature for the lateral condyle.

2. A knee prosthesis as in claim 1, wherein the shallow concave condyle surfaces of the tibial component in coronal profile have middle and side curvatures adapted to accommodate up to 5° rotational misplacement error between femoral and tibial components.

3. A knee prosthesis as in claim 1, wherein the shallow concave condyle surfaces of the tibial component in sagittal profile have sharper radii of curvature nearest anterior and posterior ends of the condyle surfaces and slighter curvature in middle portions of those condyle surfaces between the anterior and posterior ends.

4. A knee prosthesis as in claim 1, wherein the increasing anterior-to-posterior radii of curvature is a function of both patient medial-lateral (ML) and anterior-posterior (AP) dimension parameters and Fibonacci series values for successive angular quadrants of joint flexion ($\phi$), whereby the femoral condyle outer surfaces in sagittal profile approximate a logarithmic spiral.

5. A knee prosthesis as in claim 1, wherein posterior portions of each femoral condyle contacting the corresponding tibial condyle up to 90° flexion is substantially elliptical in shape, with gradually increasing radii in coronal profile as flexion increases, and anterior portions of each femoral condyle contacting the corresponding tibial condyle beyond 90° flexion is substantially spherical in shape in coronal profile with a constant radius of curvature in coronal profile equal to a radius of curvature in sagittal profile.

6. A knee prosthesis as in claim 1, wherein medial and lateral femoral condyles contact the corresponding tibial condyle at contact points tracing medial and lateral contact lines as the knee flexes, the lateral contact line being displaced further to the side compared to the medial contact line.

7. A knee prosthesis as in claim 1, wherein medial and lateral femoral condyles contact the corresponding tibial condyle at contact points tracing medial and lateral contact lines as the knee flexes, the lateral contact line being displaced further to the side compared to the medial contact line.

8. A knee prosthesis, comprising:
   a femoral joint component for attachment to a distal femur end, the femoral component having a medial condyle, a lateral condyle and an intercondylar recess between the condyles; and
   a tibial joint component for attachment to a proximal tibia end, the tibial component having shallow concave medial and lateral condyle surfaces for receiving corresponding condyles of the femoral component as bearing surfaces when the femoral and tibial components are biased together under applied tension by ligaments;
   the tibial joint component being lateral-medial mirror asymmetric in coronal profile and the shallow concave condyle surfaces of the tibial component in sagittal profile having sharper radii of curvature nearest anterior and posterior ends of the condyle surfaces and slighter curvature in middle portions of those condyle surfaces between the anterior and posterior ends, the medial and lateral condyles of the femoral joint component in sagittal profile both having spiral outer surfaces with increasing anterior-to-posterior radii of curvature, the increasing radii of curvature for the medial condyle being smaller than the corresponding radii of curvature for the lateral condyle.

9. A knee prosthesis as in claim 8, wherein the shallow concave condyle surfaces of the tibial component in coronal profile have middle and side curvatures adapted to accommodate up to 5° rotational misplacement error between femoral and tibial components.

10. A knee prosthesis as in claim 8, wherein the increasing anterior-to-posterior radii of curvature is a function of both patient medial-lateral (ML) and anterior-posterior (AP) dimension parameters and Fibonacci series values for successive angular quadrants of joint flexion ($\phi$), whereby the femoral condyle outer surfaces in sagittal profile approximate a logarithmic spiral.

11. A knee prosthesis as in claim 8, wherein posterior portions of each femoral condyle contacting the corresponding tibial condyle up to 90° flexion is substantially elliptical in shape, with gradually increasing radii in coronal profile as flexion increases, and anterior portions of each femoral condyle contacting the corresponding tibial condyle beyond 90° flexion is substantially spherical in shape in coronal profile with a constant radius of curvature in coronal profile equal to a radius of curvature in sagittal profile.

* * * * *